United States Patent [19]

Antoniades et al.

[11] Patent Number: 5,124,316
[45] Date of Patent: Jun. 23, 1992

[54] METHOD FOR PERIODONTAL REGENERATION

[75] Inventors: Harry N. Antoniades, Newton; Samuel E. Lynch, Jamaica Plain, both of Mass.

[73] Assignees: President and Fellows of Harvard College, Cambridge; Institute of Molecular Biology, Inc., Boston, both of Mass.

[21] Appl. No.: 582,332

[22] Filed: Sep. 13, 1990

Related U.S. Application Data

[63] Continuation of Ser. No. 299,763, Jan. 23, 1989, abandoned, which is a continuation-in-part of Ser. No. 234,196, Aug. 18, 1988, abandoned, which is a continuation-in-part of Ser. No. 120,606, Nov. 16, 1987, abandoned, which is a continuation-in-part of Ser. No. 930,762, Nov. 14, 1986, abandoned.

[51] Int. Cl.$^5$ .................... A61K 37/02; A61K 7/16
[52] U.S. Cl. .................... 514/12; 514/21; 514/2; 424/49; 604/54; 604/46; 604/77
[58] Field of Search .................... 514/2, 3, 21, 12; 424/101, 49; 604/54, 46, 77

[56] References Cited

U.S. PATENT DOCUMENTS 4,702,734 10/1987 Terranova .................... 604/54

FOREIGN PATENT DOCUMENTS 0312208 4/1989 European Pat. Off. .

Primary Examiner—F. T. Moezie
Attorney, Agent, or Firm—Fish & Richardson

[57] ABSTRACT

A method for promoting bone, periodontium or ligament growth of a mammal comprising applying to the bone periodontium or ligament a growth-promoting amount of a composition comprising a partially purified or purified polypeptide growth factor.

1 Claim, 1 Drawing Sheet

METHOD FOR PERIODONTAL REGENERATION

CROSS REFERENCE TO RELATED APPLICATIONS

This application is a continuation of U.S. Ser. No. 299,763, filed Jan. 23, 1989, which is a continuation-in-part of Antoniades et al., entitled "Wound Healing", U.S. Ser. No. 234,196, filed Aug. 18, 1988, which is a continuation-in-part of Antoniades et al., entitled "Wound Healing", U.S. Ser. No. 120,606, filed Nov. 16, 1987, which is a continuation-in-part of Antoniades et al., entitled "Healing External Wounds," U.S. Ser. No. 930,762, filed Nov. 14, 1986, all of which have been abandoned.

BACKGROUND OF THE INVENTION

This invention relates to the healing of bone and connective tissues.

Growth factors are polypeptide hormones which stimulate a defined population of target cells. Examples of growth factors include platelet-derived growth factor (PDGF), insulin-like growth factors (IGF-I and II), transforming growth factor beta (TGF-$\beta$), epidermal growth factor (EGF), and fibroblast growth factor (FGF). PDGF is a cationic, heat-soluble protein found in the granules of circulating platelets which is known to stimulate in vitro protein synthesis and collagen production by fibroblasts. It is also known to act as an in vitro mitogen and chemotactic agent for fibroblasts, smooth muscle cells, and glial cells.

It has been proposed to use PDGF to promote in vivo soft tissue wound healing. For example, Grotendorst (1984) J. Trauma 24:549–52 describes adding PDGF to Hunt-Schilling wire mesh chambers impregnated with a collagen gel and implanted in the backs of rats; PDGF was found to increase the amount of new collagen synthesized. However, Leitzel et al., (1985) J. Dermatol. Surg. Oncol. 11:617–22 were unable to accelerate normal wound healing in hamsters using PDGF alone or in combination with FGF and EGF.

Michaeli, et al. (1984) In *Soft and Hard Tissue Repair* (Hunt, T.K. et al., Eds), Praeger Publishers, New York, pp. 380–394, report that application of a partially purified preparation of PDGF obtained from platelet-rich plasma stimulated angiogenesis when implanted in rabbit corneas. Because PDGF is not an angiogenic growth factor the investigators suggested that an unknown factor in their partially purified PDGF preparation was responsible for the angiogenic effect.

Canalis (1985) Clin. Orthoped. Rel. Res. 193: 246–263 reports that PDGF stimulates DNA synthesis and non-specific protein synthesis in calvariae in organ culture. In contrast, Tashijian, et al. (1982), Endocrinology 111:118 report that PDGF is a potent inducer of bone resorption in mouse calveria cultures. PDGF-stimulated bone resorption was mediated through increased prostaglandin production.

SUMMARY OF THE INVENTION

In a first aspect, the invention features a method for promoting bone, periodontium or ligament growth of a mammal. The method includes applying to the bone, periodontium or ligament a growth-promoting amount of a composition containing a partially purified or purified polypeptide growth factor.

In a related aspect, the invention features promoting periodontium or ligament growth of a mammal by applying to the periodontium or ligament a growth-promoting amount of a composition containing a partially purified or purified polypeptide growth factor or a partially purified or purified differentiation factor.

By polypeptide growth factor is meant a polypeptide, including a chain of at least 6 amino acids, which modulates the growth of one or more defined populations of target cells. By differentiation factor is meant a polypeptide, including a chain of at least 6 amino acids, which stimulates differentiation of one or more defined populations of target cells into cells with cartlidge or bone forming potential.

By promoting growth is meant to include healing of a wounded bone, periodontium or ligament, and regeneration of such tissues and structures. By promoting periodontium growth is meant to include regeneration or healing of the supporting tissues of a tooth including alveolar bone, cementum and interposed periodontal ligament, which have been damaged by disease or trauma.

In preferred embodiments, the step of applying includes applying a combination of a polypeptide growth factor and a differentiation factor; the polypeptide growth factor is chosen from platelet-derived growth factor, insulin-like growth factor I or insulin-like growth factor II, transforming growth factor $\beta 1$, transforming growth factor $\beta 2$, and transforming growth factor $\alpha$; the differentiation factor is chosen from a bone morphogenetic protein (BMP) and osteogenin; most preferably the polypeptide growth factor is purified PDGF and the differentiation factor is partially purified or purified bone morphogenetic protein; the periodontium includes bone, cementum, and periodontal ligament; and the periodontium, bone, or ligament is damaged by disease or trauma, and the method includes applying to the mammal a disease-healing amount of the growth or differentiation factor.

In a related aspect, the invention features a method for preparing a composition for promoting growth of bone, periodontium or ligament. The method includes the step of mixing partially purified or purified platelet-derived growth factor in a pharmaceutically acceptable carrier substance.

In preferred embodiments, the pharmaceutically acceptable carrier substance is a natural or synthetic polymer, a bone substituting agent, or a viscous liquid or gel; most preferably the platelet derived growth factor is purified.

The compositions of this invention aid in regeneration of periodontium, at least in part, by promoting the growth of connective tissue, bone, and cementum, and by stimulating protein and collagen synthesis. Regeneration using a composition of this invention is a more effective treatment of periodontal diseases or bone wounds than that achieved using systemic antibiotics or surgical debridement alone.

In most preferred embodiments of the invention, the composition is prepared by combining partially purified or purified PDGF with a pharmaceutically acceptable carrier substance, e.g., natural and synthetic polymers (e.g., collagen, polyglycolic acid and polylactic acid), or bone substituting agents (e.g., tricalcium phosphate, hydroxyapatite, polymethylmethacrylate or demineralized freeze-dried cortical bone) or commercially available inert gels or liquids (e.g., methyl cellulose). In another most preferred embodiment, the invention features providing a composition including a combination of purified PDGF and purified BMP in a pharmaceutically acceptable carrier substance.

The factors may be obtained from human tissues or cells, e.g., platelets, or by solid phase peptide synthesis, or by recombinant DNA technology. Thus, by the term "polypeptide growth factor" or "differentiation factor", we mean tissue or cell-derived, recombinant, and synthesized materials. If the factor is a dimer, e.g., PDGF, the recombinant factor can be a recombinant heterodimer, made by inserting into cultured prokaryotic or eukaryotic cells DNA sequences encoding both subunits of the factor, and then allowing the translated subunits to be processed by the cells to form a heterodimer. Alternatively, DNA encoding just one of the subunits (e.g., for PDGF preferably the beta or "2" chain) can be inserted into cells, which then are cultured to produce homodimeric factor (e.g., PDGF-1 or PDGF-2 homodimer).

The term "purified" as used herein refers to a growth or differentiation factor, e.g., PDGF, which, prior to mixing with a carrier substance, is 95% or greater by weight, i.e., the factor is substantially free of other proteins, lipids, and carbohydrates with which it is naturally associated. The term "partially purified" refers to a lesser purity of factor, having, for example, only 5%-95% by weight of the factor, preferably 65-95%.

A purified protein preparation will generally yield a single major band on a polyacrylamide gel. Most preferably, the purified factor used in compositions of the invention is pure as judged amino-terminal amino acid sequence analysis.

The composition of the invention provides a fast, effective method for healing bony wounds of mammals, e.g., fractures, implant recipient sites, and sites of periodontal disease. The composition enhances connective tissue and bone formation compared to natural healing (i.e., no exogenous agents added) or healing supplemented by addition of systemic antibiotics. Unlike natural healing, conventional surgical therapy, or antibiotics, the composition of the above factors in a carrier prompts increased bone, connective tissue, and cementum formation when applied to periodontal disease affected sites. The restoration of these tissues leads to an improved prognosis for the affected teeth. The ability of these factors to stimulate new bone formation also makes it applicable for treating bony defects caused by other types of infection or surgical or accidental trauma.

Other features and advantages of the invention will be apparent from the following description of the preferred embodiments thereof, and from the claims.

DESCRIPTION OF THE PREFERRED EMBODIMENTS

The drawings will first briefly be described.

DRAWINGS

FIG. 1 is a diagrammatic representation of a surgical procedure for periodontium regeneration.

Figure 1A:
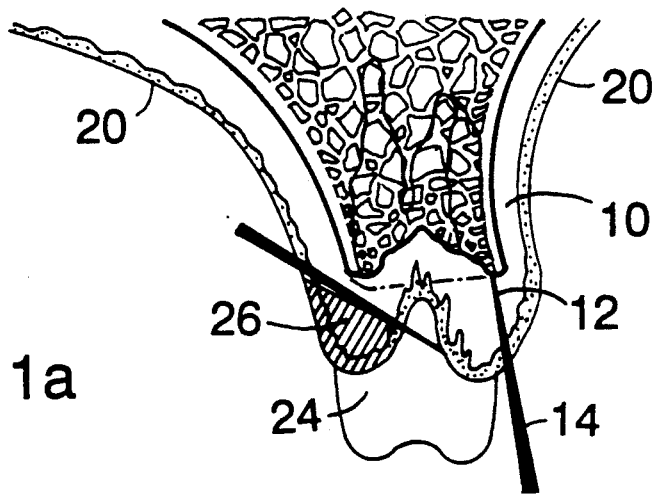

Specifically, FIG. 1A shows an area of bone around a maxillary tooth which has been depleted by periodontal disease. Bone height in the absence of disease is shown by the dashed line. The arrows show surgical incision and reflection of gingival tissue.

Figure 1B:
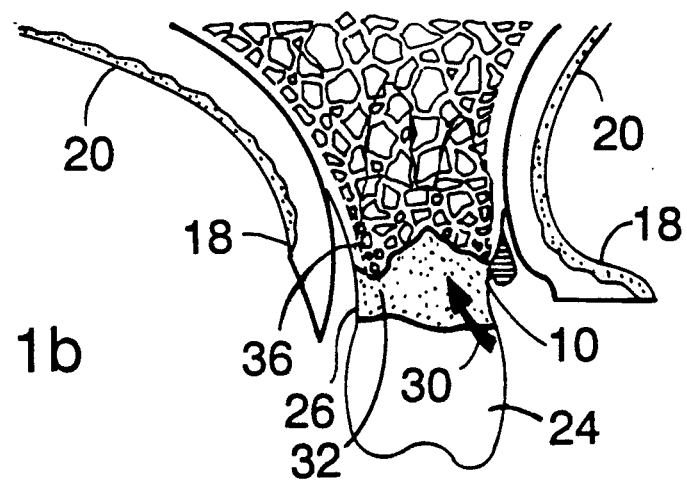

FIG. 1B shows reflection of gingival tissue to expose a tooth root surface (covered by a mineralized layer of cementum) and bone. The root surface is cleaned by root planing. The arrow indicates the approximate area where a growth and/or differentiation factor is added in a pharmaceutically acceptable carrier substance to enhance regeneration or growth of bone, cementum and the interposed periodontal ligament.

Figure 1C:
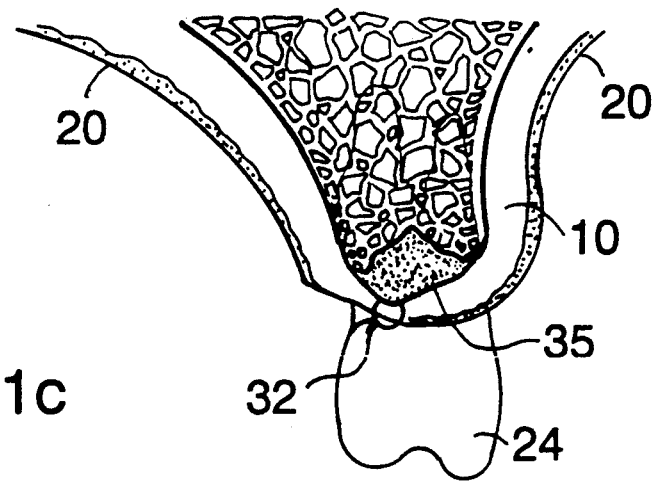

FIG. 1C, shows suturing of gingival tissue. The shaded area indicates the position of placement of a growth and/or differentiation factor.

We now describe a preferred embodiment of the invention. Below is presented an example of use of PDGF as a bone and periodontum healing agent. As described above this example is not limiting to the invention, and those skilled in the art will recognize that the invention is broadly applicable as described in the Summary of the Invention and the claims.

EXAMPLE: PDGF

Osseous wounds, e.g., following periodontal disease or trauma, are treated, and peroidontium including bone, cementum, and connective tissue regenerated, according to the invention, with PDGF prepared by combining purified PDGF with any of the pharmaceutically acceptable carrier substances described above. Purified recombinant PDGF and purified PDGF derived from human platelets are commercially available from PDGF, Inc. (Boston, Mass.), Collaborative Research (Waltham, Mass.), and Amgen Corp. (Thousand Oaks, Calif.). Partially purified and purified PDGF can also be prepared as follows:

Five hundred to 1000 units of washed human platelet pellets are suspended in 1M NaCl (2 ml per platelet unit) and heated at 100° C. for 15 minutes. The supernatant is then separated by centrifugation and the precipitate extracted twice with the 1M NaCl.

The extracts are combined and dialyzed against 0.08M NaCl-0.01M sodium phosphate buffer (pH 7.4) and mixed overnight at 4° C. with CM-Sephadex C-50 equilibrated with the buffer. The mixture is then poured into a column (5×100 cm), washed extensively with 0.08M NaCl-0.01M sodium phosphate buffer (pH 7.4), and eluted with 1M NaCl while 10 ml fractions are collected.

Active fractions are pooled and dialyzed against 0.3M NaCl-0.01M sodium phosphate buffer (pH 7.4), centrifuged, and passed at 4° C. through a 2.5×25 cm column of Blue Sepharose (Pharmacia) equilibrated with 0.3M NaCl-0.01M sodium phosphate buffer (pH 7.4). The column is then washed with the buffer and partially purified PDGF eluted with a 1:1 solution of 1M NaCl and ethylene glycol.

The partially purified PDGF fractions are diluted (1:1) with 1M NaCl, dialyzed against 1M acetic acid, and lyophilized. The lyophilized samples are dissolved in 0.8M NaCl-0.01M sodium phosphate buffer (pH 7.4) and passed through a 1.2×40 cm column of CM-Sephadex C-50 equilibrated with the buffer. PDGF is then eluted with a NaCl gradient (0.08 to 1M).

The active fractions are combined, dialyzed against 1M acetic acid, lyophilized, and dissolved in a small volume of 1M acetic acid. 0.5 ml portions are applied to a 1.2×100 cm column of Biogel P-150 (100 to 200 mesh) equilibrated with 1M acetic acid. The PDGF is then eluted with 1M acetic acid while 2 ml fractions are collected.

Each active fraction containing 100 to 200 mg of protein is lyophilized, dissolved in 100 ml of 0.4% trifluoroacetic acid, and subjected to reverse phase high performance liquid chromatography on a phenyl Bondapak column (Waters). Elution with a linear acetonitrile gradient (0 to 60%) yields pure PDGF.

PDGF made by recombinant DNA technology can be prepared as follows:

Platelet-derived growth factor (PDGF) derived from human platelets contains two polypeptide sequences (PDGF-1 and PDGF-2 polypeptides; Antoniades, H.N. and Hunkapiller, M. (1983) Science 220:963–965). PDGF-1 is encoded by a gene localized in chromosome 7 (Betsholtz, C. et al., Nature 320:695–699), and PDGF-2 is encoded by the sis oncogene (Doolittle, R. et al. (1983) Science 221:275–277) localized in chromosome 22 (Dalla-Favera, R. (1982) Science 218:686–688). The sis gene encodes the transforming protein of the Simian Sarcoma Virus (SSV) which is closely related to PDGF-2 polypeptide. The human cellular c-sis also encodes the PDGF-2 chain (Rao, C.D. et al. (1986) Proc. Natl. Acad. Sci. USA 83:2392–2396). Because the two polypeptide chains of PDGF are coded by two different genes localized in separate chromosomes, the possibility exists that human PDGF consists of a disulfide-linked heterodimer of PDGF-1 and PDGF-2, or a mixture of the two homodimers (homodimer of PDGF-1 and homodimer of PDGF-2), or a mixture of the heterodimer and the two homodimers.

Mammalian cells in culture infected with the Simian Sarcoma Virus, which contains the gene encoding the PDGF-2 chain, were shown to synthesize the PDGF-2 polypeptide and to process it into a disulfide-linked homodimer (Robbins et al. (1983) Nature 305:605–608). In addition, PDGF-2 homodimer reacts with antisera raised against human PDGF. Furthermore, the functional properties of the secreted PDGF-2 homodimer are similar to those of platelet-derived PDGF in that it stimulates DNA synthesis in cultured fibroblasts, it induces phosphorylation at the tyrosino residue of a 185 kd cell membrane protein, and it is capable of competing with human ($^{125}$I)-PDGF for binding to specific cell surface PDGF receptors (Owen, A. et al. (1984) Science 225:54–56). Similar properties were shown for the sis/PDGF-2 gene product derived from cultured normal human cells (for example, human arterial endothelial cells), or from human malignant cells expressing the sis/PDGF-2 gene (Antoniades, H. et al. (1985) Cancer Cells 3:145–151).

The recombinant PDGF-2 homodimer is obtained by the introduction of cDNA clones of c-sis/PDGF-2 gene into mouse cells using an expression vector. The c-sis/PDGF-2 clone used for the expression was obtained from normal human cultured endothelial cells (Collins, T., et al. (1985) Nature 216:748–750).

PERIODONTAL AND BONE REGENERATION

To determine the effectiveness of PDGF in promoting periodontium and bone growth, the following experiments were performed.

Six year old beagle dogs (Laboratory Research Enterprises, Kalamazoo, Mich.) with naturally occurring periodontal disease were selected on the basis of an initial radiographic examination of their teeth. Teeth which exhibited 20% to 80% reduction of surrounding jaw bone were initially scaled using ultrasonic instruments. Referring to FIG. 1, an example of such reduction is shown, where a diseased jaw bone 10 (the extent of a normal bone is shown by dashed line 12) exhibits about 20% reduction in size due to the disease. A conventional gingival full thickness surgical flap 18 is then produced by an incision, shown at arrow 14, and 16.

This removes gingiva 20 from around jaw bone 10 and tooth 24. Root 26 of the tooth is then planed to remove bacterial plaque and calculus. The experimental teeth were treated by the topical application of 500 ng to 5 mg, but generally one microgram of purified PDGF per tooth in a pharmacuetically acceptable carrier substance, e.g., a commercially available inert gel such as methyl cellulose, as shown by arrow 30. Generally, the PDGF is applied to the root of the tooth at the point where the cementum has been planed. It is thus near or adjacent cementum 32, bone 10, and interposed periodontal ligament (not shown). The remaining teeth received the carrier alone. The gingival flap was then placed back to near its original position and held together by a suture 32. The position of the PDGF-containing methyl cellulose is shown by shaded area 35.

Block biopsies of the teeth and surrounding bone were taken at two weeks post-treatment and prepared for histologic evaluation using standard demineralizing (10% trifluoroacetic acid) and processing techniques. Sections were stained with hematoxylin and eosin to allow old and new bone cementum and periodontal ligament to be differentiated.

RESULTS

Results of histologic analyses of periodontal and bone specimens indicated that, in PDGF-treated specimens: a) new bone was formed adjacent the root surfaces, b) a deposit resembling cementum was formed on the root surface adjacent the new bone, c) new bone was also formed on the periosteal and endosteal surfaces of the specimens, —d) evidence of ankylosis (fusion of bone and root surfaces) due to bone growth was present within the apical extent of the periodontal ligament, e) a dense layer of osteoblasts lined the newly formed bone, f) some osteoblasts were incorporated into the forming bone and formed osteocytes, g) a dense band of osteoblast-like cells was present within the connective tissue immediately coronal to the area of newly forming bone, and h) newly formed collagen fibers were observed inserting into the newly formed cementum deposits on the root surface. Thus, in treated sites, periodontal regeneration was occurring, including reformation of bone, connective tissue (periodontal ligament), and cementum.

In the control specimens there was no evidence of new bone formation, and there was an absence of new cementum-like deposits. Gingival connective tissue immediately coronal to the alveolar bone was oriented perpendicular to the bony surface appearing to form a "cap" over the original bone. There was no sign of any periodontal regeneration occurring. This is the first time that a purified polypeptide growth or differentiation factor, such as PDGF, has been demonstrated to enhance periodontal regeneration. These results indicate that the composition of the invention enhances osteogenic, cementogenic, and connective tissue responses.

USE

PDGF alone or in combination with other growth factors is useful for promoting bone healing, bone growth and regeneration or healing of the supporting structures of teeth injured by trauma or disease. It is also useful for promoting healing of a site of extraction of a tooth, for mandibular ridge augmentation, or at tooth implant sites. Bone healing would also be enhanced at sites of bone fracture or in infected areas, e.g., osteomyelitis, or at tumor sites. PDGF is also useful for promoting growth and healing of a ligament, e.g., the periodontal ligament, and of cementum.

In use, the PDGF or other growth or differentiation factor is applied directly to the area needing healing or regeneration. Generally, it is applied in a resorbable or non-resorbable carrier as a liquid or solid, and the site then covered with a bandage or nearby tissue. An amount sufficient to promote bone growth is generally between 500 ng and 5 mg for a 1 cm$^2$ area, but the upper limit is really one of for a 1 cm$^2$ area, but the upper limit is really one of expense of the PDGF, and is not a physiological limit.

Other embodiments are within the following claims.

We claim:

1. A method of promoting growth of damaged bone, periodontium, or ligament of a living mammal, comprising the steps of producing a surgical flap of skin to expose said damaged bone, periodontium, or ligament, planing said damaged bone or periodontium to remove organic matter from said bone or periodontium applying platelet derived growth factor in a pharmaceutically acceptable carrier to said exposed bone, periodontium, or ligament, replacing said flap, and allowing said damaged bone, periodontium, or ligament to regrow.

* * * * *

UNITED STATES PATENT AND TRADEMARK OFFICE
CERTIFICATE OF CORRECTION

PATENT NO. : 5,124,316

DATED : June 23, 1992

INVENTOR(S) : Harry N. Antoniades, et al

It is certified that error appears in the above-identified patent and that said Letters Patent is hereby corrected as shown below:

Column 1, line 26, change "heat-soluble protein" to --heat-stable protein--;

Column 2, line 11, correct the spelling of "cartilage";

Column 7, lines 11-12, delete the following: --for a 1 $cm^2$ area, but the upper limit is really one of--.

Signed and Sealed this

Sixteenth Day of November, 1993

*Attest:*

BRUCE LEHMAN

*Attesting Officer*   *Commissioner of Patents and Trademarks*